United States Patent
Kim et al.

(10) Patent No.: US 9,714,207 B2
(45) Date of Patent: Jul. 25, 2017

(54) METHOD FOR PRODUCING AROMATIC COMPOUND FROM BIOMASS-DERIVED ACETIC ACID

(71) Applicant: SK INNOVATION CO., LTD., Seoul (KR)

(72) Inventors: Hee Soo Kim, Daejeon (KR); Ho Won Lee, Daejeon (KR); Seon Ju Lim, Daejeon (KR); Dong Ryul Park, Daejeon (KR)

(73) Assignee: SK INNOVATION CO., LTD., Seoul (KR)

( * ) Notice: Subject to any disclaimer, the term of this patent is extended or adjusted under 35 U.S.C. 154(b) by 0 days.

(21) Appl. No.: 14/896,141

(22) PCT Filed: Jun. 3, 2014

(86) PCT No.: PCT/KR2014/004945
§ 371 (c)(1),
(2) Date: Mar. 31, 2016

(87) PCT Pub. No.: WO2014/196791
PCT Pub. Date: Dec. 11, 2014

(65) Prior Publication Data
US 2016/0221906 A1    Aug. 4, 2016

(30) Foreign Application Priority Data
Jun. 5, 2013 (KR) .................. 10-2013-0064631

(51) Int. Cl.
*C07C 1/207* (2006.01)
*C07C 6/12* (2006.01)
(Continued)

(52) U.S. Cl.
CPC ........... *C07C 45/74* (2013.01); *B01J 23/6484* (2013.01); *B01J 35/006* (2013.01); *C07C 1/2076* (2013.01);
(Continued)

(58) Field of Classification Search
CPC ... B01J 23/6484; B01J 35/006; C07C 1/2076; C07C 45/54; C07C 45/66; C07C 45/74;
(Continued)

(56) References Cited

U.S. PATENT DOCUMENTS 5,968,343 A    10/1999   Drake et al.
6,867,340 B2   3/2005    Oh et al.
(Continued)

FOREIGN PATENT DOCUMENTS

KR   10-2001-0012146 A   2/2001
KR   10-2012-0009689 A   2/2012
(Continued)

OTHER PUBLICATIONS

International Search Report for PCT/KR2014/004945 dated Sep. 29, 2014 (2 pages).
(Continued)

*Primary Examiner* — Medhanit Bahta
(74) *Attorney, Agent, or Firm* — Abelman, Frayne & Schwab (57) ABSTRACT

In a specific example according to the present invention, a method is disclosed in which a catalytic reaction is used in order to convert acetic acid, which has been produced by the biological processing or physicochemical processing of biomass, into an aromatic compound constituting a raw material for a high-added-value product such as BTX and, more particularly, p-xylene.

26 Claims, 7 Drawing Sheets

(51) Int. Cl.
 *C07C 51/41* (2006.01)
 *C07C 45/74* (2006.01)
 *C12P 7/22* (2006.01)
 *B01J 23/648* (2006.01)
 *B01J 35/00* (2006.01)
 *C07C 45/66* (2006.01)
 *C07C 45/54* (2006.01)

(52) U.S. Cl.
 CPC .............. *C07C 6/126* (2013.01); *C07C 45/54* (2013.01); *C07C 45/66* (2013.01); *C07C 51/412* (2013.01); *C12P 7/22* (2013.01); *C07C 2101/16* (2013.01); *C07C 2523/648* (2013.01); *Y02P 20/52* (2015.11)

(58) Field of Classification Search
 CPC ... C07C 51/412; C07C 6/126; C07C 2101/16; C07C 2523/648; C12P 7/22; Y02P 20/52
 See application file for complete search history.

(56) References Cited

U.S. PATENT DOCUMENTS

| | | | |
|---|---|---|---|
| 8,679,805 | B2 | 3/2014 | Chung et al. |
| 2010/0048381 | A1 | 2/2010 | Oh et al. |
| 2012/0203042 | A1 | 8/2012 | Huber et al. |
| 2013/0079566 | A1 | 3/2013 | Lin |
| 2013/0210106 | A1 | 8/2013 | Chung et al. |

FOREIGN PATENT DOCUMENTS

| | | |
|---|---|---|
| KR | 10-2012-0041578 A | 5/2012 |
| KR | 10-2012-0104520 A | 9/2012 |

OTHER PUBLICATIONS

Sandeep D. Randery, et al., "Cerium oxide-based catalysts for production og ketones by acid condensation," Applied Catalysts A: General, 226:265-280 (2002).

K. S. Kim, et al., "Structure and Composition Requirements for Deoxygenation, Dehydration,a nd Ketonization Reactions of Carboxylic Acids on TiO2(oo1) Single-Crystal Surfaces," Journal of Catalysis, 125:353-375 (1990).

R. Pestman, et al., "Reactions of Carboxylic Acids on Oxides—2. Bimolecular Reaction of Aliphatic Acids to Ketones," Journal of Catalysis, 168:265-72 (1997), Dec. 13, 2016.

Tu Nguyuet Pham, et al., "Aqueous-phase ketonization of acetic acid over Ru/TiO2/carbon catalysts," Journal of Catalysis, 295:169-179 (2012).

| Products | Selectivity % |
|---|---|
| Acetone | 86.3 |
| Acetic acid | 0.2 |
| 2-Butanone | 0.4 |
| 3 methyl 2 pentanone | 0.2 |
| 4 methyl 3 penten 2 one | 4.4 |
| 1,3,5 TMB | 1.5 |
| 2 Cyclohexene 1-one | 1.5 |
| 3,5 dimethyl phenol | 2.6 |
| The Others | 1.9 |

METHOD FOR PRODUCING AROMATIC COMPOUND FROM BIOMASS-DERIVED ACETIC ACID

CROSS REFERENCE TO RELATED APPLICATION

This application is a §371 of PCT/KR2014/004945 filed Jun. 3, 2014, and claims the benefit of Korean Patent Application No. 10-2013-0064631, filed Jun. 5, 2013, both are hereby incorporated by reference in their entirety into this application.

TECHNICAL FIELD

The present invention relates to a method for converting acetic acid into aromatics useful as raw materials for high value-added aromatic products. More particularly, the present invention relates to a method for producing aromatics convertible into high value-added aromatic products such as benzene/toluene/xylene (BTX), particularly para-xylene (p-xylene), from the acetic acid that is biologically or physicochemically derived from biomass.

BACKGROUND ART

For the production of chemical products from biomass, various methods have been suggested such as entirely biological methods using anaerobic fermentation, and mixed methods in which intermediates obtained through biological pretreatment are chemically converted into high value-added products. On the whole, the application of biological methods to biomass means that hydrocarbons obtained from biomass by pretreatment are converted by microbial fermentation. For example, carbohydrates in biomass are converted into fermentable sugars from which ethanol, butanol, organic acids, and various amino acids can be produced by ethanol fermentation. As such, various attempts have been made to utilize biomass-derived compounds in producing higher value-added materials. Most biomass-derived compounds are obtained with an excess of water contained therein, that is, as an aqueous solution. In order to produce a target compound, water is usually separated before subsequent conversion reactions. However, the separation of water requires a significant amount of energy and additional processes, which is undesirable in view of process efficiency and economy.

Typically, benzene/toluene/xylene, known as high value-added aromatic products, are generally produced by hydrotreating and extracting pyrolysis gasoline. The production of benzene/toluene/xylene, together with basic fraction products such as ethylene, propylene and the like, occurs during the thermal cracking process of naphtha, or by catalytically reforming naphtha to form reformates, followed by separating them. In the case of using naphtha, which is produced with a narrow boiling point range in an atmospheric distillation process, conventional production techniques of aromatic products cannot smoothly respond to increasing demand. Meanwhile, the production of aromatic products from raw petroleum materials is highly apt to be accompanied with the production of environmental pollution due to a significant content of impurities such as sulfur, nitrogen, etc. in the raw materials.

To avoid this problem, the use of biomass in producing aromatic products, particularly BTX products, has been attempted. For example, biomass is thermally decomposed, and the pyrolyzates are reacted in the presence of a catalyst to yield olefins and aromatics (Korean Patent Unexamined Application Publication No. 2012-0104520). In this regard, catalytic fast pyrolysis (CFP) has been suggested as an advanced process. According to CFP, biomass is fed into a fluidized bed reactor where pyrolysis is conducted to form a pyrolysis steam, followed by introducing the pyrolysis steam into the zeolite catalyst bed in the fluidized bed reactor to produce aromatics and olefins.

In this context, the present applicant suggested a method in which ketone compounds are converted from mixed organic acids and then prepared into fuels, lubricant base oils, and aromatics through catalytic reactions (Korean Patent No. 2012-41578). The method disclosed in this patent reference is a technique for producing various hydrocarbons from ketone compounds by condensation, hydrogenation, and/or hydrodeoxygenation in the presence of a hydrogenation catalyst. Particularly since presenting a reaction mechanism by which a series of catalytic reactions can be conducted even in an aqueous solution, the method can bring about an improvement in process yield and economy. As is identified in the Examples thereof, the final product obtained by the method contains paraffins at a content of about 90 mol % or more, but aromatics at a level as low as impurities (around 5 mol %). Accordingly, the method is substantially directed toward the preparation of fuels and lubricant base oils made of paraffins, but is difficult to apply to improvement in the yield of aromatics.

As such, there is a need for a detailed technique (e.g., controlling catalyst and process conditions) by which the production yield of aromatics can be improved to a degree of significance on the basis of a reaction route feasible even in an aqueous solution.

DISCLOSURE

Technical Problem

One embodiment according to the present invention is to provide a process for effectively converting acetic acid, particularly biomass-derived acetic acid into an aromatic compound useful as a raw material for high value-added aromatics.

In addition, another embodiment according to the present invention is to provide a method for producing an aromatic compound from biomass-derived acetic acid in which biomass-derived acetic acid in an excess of water is converted into acetone by ketonization, followed by conversion into aromatics useful as raw materials for high value-added aromatic products through aldol-condensation, hydrodeoxygenation, and cyclization in the presence of an catalyst.

Technical Solution

In accordance with an aspect thereof, the present invention provides a method for producing an aromatic compound from acetic acid, comprising:

a1) providing acetic acid;
b1) converting the acetic acid into acetone; and
c1) converting the acetone into an aromatic compound in the presence of a ruthenium-supported niobia catalyst (Ru/Nb);

wherein the ruthenium-supported niobia catalyst (Ru/Nb) contains ruthenium in an amount of 0.3 to 2.5% by weight on an elemental basis.

In one embodiment, the acetic acid may be biomass-derived acetic acid.

In accordance with another aspect thereof, the present invention provides a method a for an aromatic compound from biomass-derived acetic acid, comprising:

a2) providing an aqueous solution containing the biomass-derived acetic acid;

b2) reacting the aqueous solution containing the biomass-derived acetic acid in presence of a catalyst to give an acetone-containing aqueous solution; and c2) converting the acetone of the acetone-containing aqueous solution into an aromatic compound in presence of a ruthenium-supported niobia catalyst (Ru/Nb); and d2) separating water from the product of step c2) to recover the aromatic compound, wherein the ruthenium-supported niobia catalyst (Ru/Nb) contains ruthenium in an amount of 0.3 to 2.5% by weight on an elemental basis.

In step d2), an aromatic compound can be recovered from the product of step c2) by phase separation.

In one embodiment, steps b1) and c1), and steps b2) and d2) may be carried out in a single reactor consecutively and/or successively.

According to an exemplary embodiment, the conversion of acetone into aromatics may be achieved by aldol-condensation, hydrodeoxygenation, and cyclization (these reactions may be carried out in a single step). In this regard, at least two rounds of the aldol-condensation may be carried out.

According to an exemplary embodiment, the aromatic compound produced by the method may be a monocyclic aromatic compound of 6 to 13 carbon atoms.

According to an exemplary embodiment, the method may further comprise subjecting the aromatic compound produced in step c1) or d2) into trans-alkylation to afford benzene/toluene/xylene, particularly xylene (mixed xylene), and more particularly p-xylene.

Advantageous Effects

According to one embodiment of the present invention, the acetic acid obtained from biomass by biological (e.g., fermentation) or physicochemical treatment (e.g., hydrothermal treatment) is reacted through a novel route to produce an aromatic compound convertible into a high value-added aromatic product, such as BTX, particularly p-xylene, at high conversion rate and selectivity. Because it is based on petroleum such as naphtha, but derived from a novel origin, that is, biomass, the aromatic compound useful for the production of high value-added aromatic products can be obtained in a great amount. Further, the method of the present invention does not produce environmental pollutants, such as sulfur, nitrogen, etc. Moreover, the method of the present invention does not require an additional process of separating or recovering acetone because it allows a series of catalytic reactions to be carried out without removing water from the aqueous acetic acid solution. In a specific embodiment, the acetone converted from biomass-derived acetic acid can be converted into aromatics through aldol-condensation, hydrodeoxygenation and cyclization while the conversion rate of acetone and selectivity for acetone can be maximized by controlling process conditions (temperature, pressure, hydrogen flow rate, etc.) for a given catalyst. Accordingly, the method of the present invention is expected to be used in commercializing various aromatics.

BEST MODE

The present invention may be accomplished by the following description. The following description should be understood to illustrate the present invention, but is not given as limiting the present invention.

The terms used herein are defined as follows.

The term "biomass" refers generally to an organic material produced by photosynthesis and may be widely understood to encompass organic wastes such as livestock excretions, food wastes, etc. In the present invention, biomass may be intended to encompass various biological resources known in the art, including plant biomass, such as cellulose, hemicelluloses and/or lignin (e.g., lignocelluloses). Representative of the biomass are plant sources such as corns, beans, linseeds, sugar cane, and palm oil. Examples of the biomass available for the present invention include rice straw, wheat straw, starch-containing cereals, corncobs, corn stalks, rice bran, paper products, woods, sawdust, agricultural wastes, lawn, sugar cane, cotton, flax, bamboo, Manila hemp, algae, fruit skins, seaweeds, palm wastes, plant stalks, roots and leaves.

As used herein, the term "biomass-derived acetic acid" means the acetic acid obtained from acetic acid by biological treatment (typically fermentation) or physicochemical treatment (e.g., hydrothermal treatment).

As used herein, the term "aromatics" refers to aromatic compounds that can be converted into the high value-added aromatic product benzene/toluene/xylene (BTX), particularly p-xylene. In the present invention, an aromatic refers to a monocyclic aromatic compound that can be converted into BTX by a subsequent process (e.g., transalkylation). Strictly, hence, fused polycyclic aromatic compounds (for example, indane in which a benzene ring and cyclopentane are fused, and naphthalene in which two benzene rings are fused) may be excluded from the scope of target compounds of the present invention.

The term "naphthenic compound," as used herein, means, in a broad sense, an alkane compound having at least one ring. Naphthenic compounds that are considered together with an aromatic upon assessing a degree of selectivity may be monocyclic alkane compounds that result from the removal of double bonds of monocyclic aromatics by hydrogenation.

Outline of Overall Processes

Figure 1:
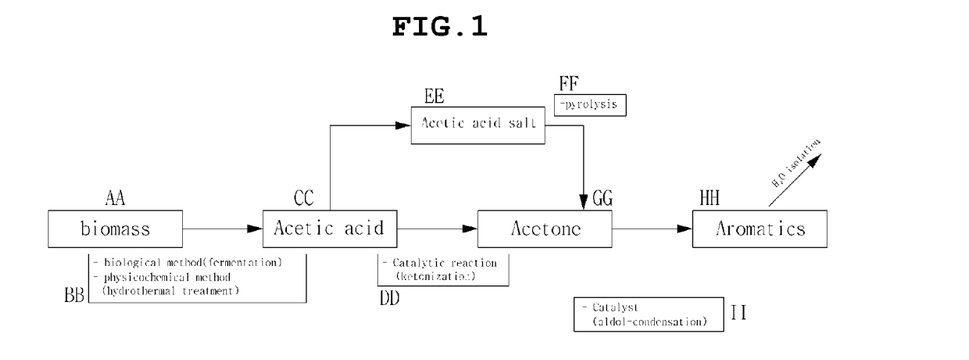
FIG. 1 is a schematic process configuration illustrating a series of process steps for producing aromatics from biomass via acetic acid and acetone in accordance with an embodiment of the present invention.

FIG. 1 is a schematic process configuration illustrating a series of process steps for producing aromatics from biomass via acetic acid and acetone. As can be seen, the acetic acid prepared from biomass by biological treatment (fermentation) or physicochemical treatment (hydrothermal treatment) may be a starting material in one embodiment of the present invention. Of course, the embodiments of the present invention are not limited to biomass-derived acetic acid. As illustrated in accordance with an embodiment of the present invention, the acetic acid typically is in an aqueous solution when obtained by the treatment, and (i) is converted into an acetate, followed by the formation of acetone through pyrolysis (accompanied by the separation of acetic acid from water), or (ii) is converted into acetone by a catalytic reaction (ketonization) without additionally separating acetic acid from the aqueous solution. Thereafter, the acetone (aqueous acetone solution) thus obtained is selectively converted into an aromatic in the presence of a catalyst. In this regard, conversion into aromatics is accomplished typically by aldol-condensation, hydrodeoxygenation and cyclization.

In one embodiment, the conversion of acetic acid into acetone and the aromatization of acetone may be performed in a single reactor consecutively and/or successively.

Provision of Acetic Acid (or Biomass-Derived Acetic Acid)

Acetic acid is produced, for the most part, in an industrial process via various routes including microbial fermentation from inexpensive raw materials such as biomass. In one embodiment of the present invention, acetic acid may be prepared from biomass biologically or physicochemically. Representative of the biological method and the physicochemical method are fermentation and hydrothermal treatment, respectively. Because both the fermentation and the hydrothermal treatment are typically performed in the presence of water, the acetic acid thus obtained contains an excess of water (e.g., exists as an aqueous solution).

According to an exemplary embodiment, the concentration of acetic acid in the aqueous solution varies depending on the conditions of fermentation or hydrothermal treatment (e.g., amount of water). For example, the concentration may range from about 1 to 90% by weight, preferably from about 1 to 50% by weight, and more preferably from about 1 to 10% by weight. In addition, the aqueous acetic acid solution may have a pH of, for example, about 2 to 6, particularly about 2 to 4, and more particularly about 2 to 3.

Fermentative Production of Acetic Acid

In one embodiment, so long as it is well known in the art, any fermentative process of converting biomass into acetic acid may be available without particular limitations. For example, ethanol may be associated with oxygen in the presence of a microbial strain, or acetic acid may be obtained by the anaerobic fermentation of food wastes or livestock excretions.

According to an exemplary embodiment, biomass is introduced into a reactor where anaerobic fermentation occurs with the concomitant production of acetic acid. Examples of strains available for the production of acetic acid include *Saccharomoyces cerevisiae*, which is typically used to produce ethanol from monosaccharides, and modified strains thereof. However, so long as it is able to produce acetic acid, any strain may be available without limitations. In order to produce acetic acid through anaerobic fermentation, biomass is first pretreated by, for example, crushing. Then, the pretreated biomass material is fed, together with water, to an acid fermenter where aerobic fermentation is performed at a certain temperature (e.g., about 30 to 50° C., particularly about 40 to 50° C.) for a predetermined period of time (e.g., about 12 to 72 hrs, particularly about 24 to 56 hrs) in the presence of an acetic acid-producing strain. With the progression of the fermentation, an aqueous acetic acid solution is obtained. If the fermentation excessively proceeds, acetic acid may be converted into methane and carbon dioxide. Accordingly, it is desired to control the fermentation condition.

Production of Acetic Acid by Hydrothermal Treatment

A basic principle of the production of acetic acid by hydrothermal treatment is described in Korean Patent Application No. 2012-37060 (not publicized) to the present applicant, which is hereby incorporated by reference in its entirety into this application.

According to an exemplary embodiment, the biomass may be allowed to undergo mechanical pretreatment advantageous for conversion into acetic acid prior to hydrothermal treatment. As used herein "mechanical pretreatment" is a concept used to encompass any physical or mechanical manipulation of reducing the size of biomass, such as cutting, compression, impaction, ablation, shearing, etc. After the mechanical pretreatment, the biomass may range in size from micrometers to centimeters. Even a pellet type of biomass has no significant influence on the hydrothermal treatment. Because not undergoing a fermentation process, the hydrothermal treatment requires a relative short time for the production of acetic acid. Further, the hydrothermal treatment can produce acetic acid in consecutive processes, and can be applied to the conversion into acetic acid of lignin and hemicellulose, which are difficult to covert by fermentation. Apparatuses available for hydrothermal treatment may be exemplified by single screw extruders, twin screw extruders, batch extruders, batch-type kneaders, batch-type high-temperature reactors. Other apparatuses suitable for converting into acetic acid may be also used.

Meanwhile, hydrothermal treatment may be typically conducted under the condition of supplying water or steam. The water (steam) used for the hydrothermal treatment may range from about 10 to 90% by weight based on the total weight of the biomass, particularly from about 30 to 80% by weight, and more particularly from about 50 to 70% by weight. In addition, the reaction time of hydrothermal treatment may be determined in consideration of the volume of the reactor and the length and diameter of the screw employed in the extruder. For example, the reaction time may be about 1 to 60 min, particularly about 5 to 40 min, and more particularly about 10 to 30 min.

According to one embodiment, the hydrothermal treatment may be conducted at, for example, about 100 to 370° C. (particularly, about 200 to 320° C., more particularly, about 240 to 300° C.) under a pressure of about 1 to 220 bar (particularly about 20 to 150 bar, more particularly about 50 to 100 bar (a subcritical conditions). Optionally, a supercritical condition (particularly, about 372° C. or higher, and about 221 bar or higher) may be employed.

The mechanism of converting biomass into acetic acid is difficult to explain in the same light because a mixture of cellulose, hemicellulose and lignin in biomass is treated at once with the consequent accompaniment of various reactions. Without being limited to a certain theory, the production of acetic acid in accordance with the present invention may be achieved in such a manner that cellulose and hemicelluloses are decomposed into oligosaccharides and then further into monosaccharides such as glucose and fructose, followed by converting fructose into aldehydes that are subsequently oxidized into acetic acid. Optionally, a purification step known in the art may be conducted to enrich the acetic acid in the aqueous solution. For example, the concentration of acetic acid may be increased by use of a membrane according to molecular size, crosslinking of carboxyl anions, etc.

When produced in the above-mentioned process, the acetic acid is obtained as an aqueous solution. For separating acetic acid from water, distillation or extraction is typically used. However, the former is problematic in that acetic acid and water are not significantly different in boiling point, with azeotropy existing therebetween. For the latter, the extracting agent should be additionally separated. A membrane separation technique known in the art may be advantageous in terms of separation efficiency, but disadvantageous in terms of cost. Accordingly, a subsequent process is preferred without separating water from the aqueous acetic solution. As illustrated later, the separation of water from the aqueous acetic acid is necessarily required.

Production of Acetone from Acetic Acid

Catalytic Concertion

In one embodiment, acetic acid (biomass-derived acetic acid) may be converted into acetone in the presence of a catalyst. For this, water may be selectively removed from the aqueous acetic acid solution and the acetic acid thus recovered may be subjected to a catalytic reaction for conversion into acetone (ketonization). However, the aqueous acetic acid solution itself is advantageously brought into a catalytic reaction in light of process efficiency and economy.

The mechanism of converting acetic acid into acetone through a catalytic reaction is known in the art as disclosed in, for example, Journal of Catalysis, 295 (2012) 169, D. E. Resasco; Journal of Catalysis, 125 (1990) 353, K. S. Kim; Journal of Catalysis, 168 (1997) 265; Applied Catalysis A 226 (2002) 265, S. D. Randery, which are hereby incorporated by reference in their entireties into this application.

The catalyst useful in the reaction includes zirconia, titania, alumina, silica, silica-alumina, and a combination thereof. Particularly, zirconia is active for ketonization into acetone. Such a ketonization catalyst may be prepared using a precipitation method. For example, a zirconia catalyst may be from a zirconium precursor such as zirconium nitrate, zirconium carbonate, zirconium chlorinate, etc. In detail, a zirconium precursor is dissolved in an aqueous solution (e.g., a concentration of about 1 to 30% by weight) and treated with a precipitating agent, followed by filtrating separation/purification/sintering to yield a zirconia catalyst. Typical among the precipitating agents useful in the reaction are alkaline precipitating agents, for example, NaOH, $Na_2CO_3$, and $NH_4OH$. During the precipitation, the solution in which the zirconia precursor and the precipitating agent has a final pH of, for example, about 2 to 11, particularly about 4 to 9, and more particularly about 6 to 8. The precipitate thus obtained is filtered, purified (with distilled water), and sintered. The sintering temperature may be set to be, for example, about 300 to 700° C., particularly about 400 to 600° C., and more particularly about 400 to 500° C.

For the catalytic reaction, one molecule of acetone is formed from two molecules of acetic acid as illustrated by the following Reaction Scheme.

[Reaction Scheme 1]

A temperature suitable for the ketonization may range from, for example, about 200 to 600° C., particularly from about 250 to 500° C., and more particularly from 300 to 450° C. Meanwhile, the ketonization may be carried out in a broad range of pressures, for example, under a pressure of about 0.05 to 50 bar, particularly about 0.5 to 30 bar, and more particularly about 1 to 15 bar. In addition, when the ketonization is operated in a continuous mode, the space velocity (WHSV) may range, for example, from about 0.1 to 10 $h^{-1}$, particularly from about 0.5 to 5 $h^{-1}$, and more particularly from about 1 to 2 $h^{-1}$. For a batch-type reaction, the ketonization catalyst may be used in an amount of about 0.01 to 2 g based on 100 cc of the reactant (acetic acid), and particularly in an amount of about 0.1 to 1 g.

In accordance with one embodiment, the ketonization may exhibit a conversion rate of acetic acid of at least about 70% and particularly about 80 to 99%, and a selectivity for acetone of at least about 60%, and particularly about 70 to 99%.

When an aqueous acetic acid solution is used as a reactant, the product acetone is obtained as an aqueous solution because of its high miscibility with water. For the aromatization of acetone, as will be explained later, the aqueous acetone solution may be used as it is. In this regard, the aqueous solution has an acetone concentration of, for example, about 1 to 90% by weight, particularly about 5 to 70% by weight, and more particularly about 10 to 50% by weight.

Pyrolytic Conversion of Acetate

According to an alternative embodiment, an aqueous acetic acid solution having an excess of water is converted into acetate (particularly metal salt) that is then recovered by removing water. The recovered acetate is converted into acetone by pyrolysis. the reaction mechanism may be illustrated as shown in the following Reaction Scheme 2.

[Reaction Scheme 2]

-continued

In this Reaction Scheme, a cationic metal for use in producing metal salts of acetic acid may be an alkali metal and/or alkaline earth metal. Examples of available cationic metals include Na, K, Mg, Be, and Ca, with preference for Ca. According to an exemplary embodiment, the acetate recovered can be converted into acetone by pyrolysis at, for example, about 300° C. or higher, particularly at about 350 to 500° C., and more particularly at about 400 to 450° C.

At a lower temperature of the pyrolysis, it takes a longer time to complete the conversion. On the other hand, a higher temperature of the pyrolysis allows for the more extensive production of by-products such as phenols. During the pyrolysis, three or more acetic acid molecules in addition to two molecules may react. The ketones of three or more carbon atoms can be reactants for conversion into aromatics. In one exemplary embodiment, the reactant acetate may be converted into acetone at a rate of at least about 50% by weight, particularly about 60 to 90% by weight, with a selectivity for acetone of about 70% by weight, particularly about 80 to 90% by weight. By-products produced during the pyrolysis can be separated and removed from acetone by, for example, distillation.

Aromatization of Acetone

In accordance with an embodiment of the present invention, the acetone obtained from by catalytic ketonization or from acetate by pyrolysis may be converted into an aromatic compound in the presence of a catalyst under a condition of supplying hydrogen. The reactant acetone may be in an aqueous solution phase or in a dehydrated state. The production yield of aromatics useful as raw materials for BTX (particularly para-xylene) may be increased by controlling reaction conditions including catalysts.

In one exemplary embodiment, the aqueous acetone solution (e.g., not separated from water) may be converted into aromatics (convertible into BTX, particularly para-xylene) in the presence of a solid acid catalyst supported with metal hydride. When an aqueous acetone solution is used as a reactant, it has an acetone concentration of, for example, about 1 to 90% by weight, particularly about 5 to 70% by weight, and more particularly about 10 to 50% by weight.

An advantage of this embodiment is to conduct a series of processes for producing aromatics from the starting material acetic acid through acetone without removing an excess of water (that is, separating a product in each step from water). This is preferable in technical and economical points of view. Particularly, the production of aromatics applicable to high value-added aromatic products from biomass of various sources may be an alternative solution to the increasing current demand on aromatic products.

According to one embodiment, aldol-condensation, hydrodeoxygenation and/or cyclization is conducted to convert acetone into an aromatic compound. These reactions may occur in a single catalytic reaction. A series of reaction mechanisms for the aromatization of acetone are schematically illustrated, together with the production mechanisms of other by-products, in FIG. 2.

Figure 2:
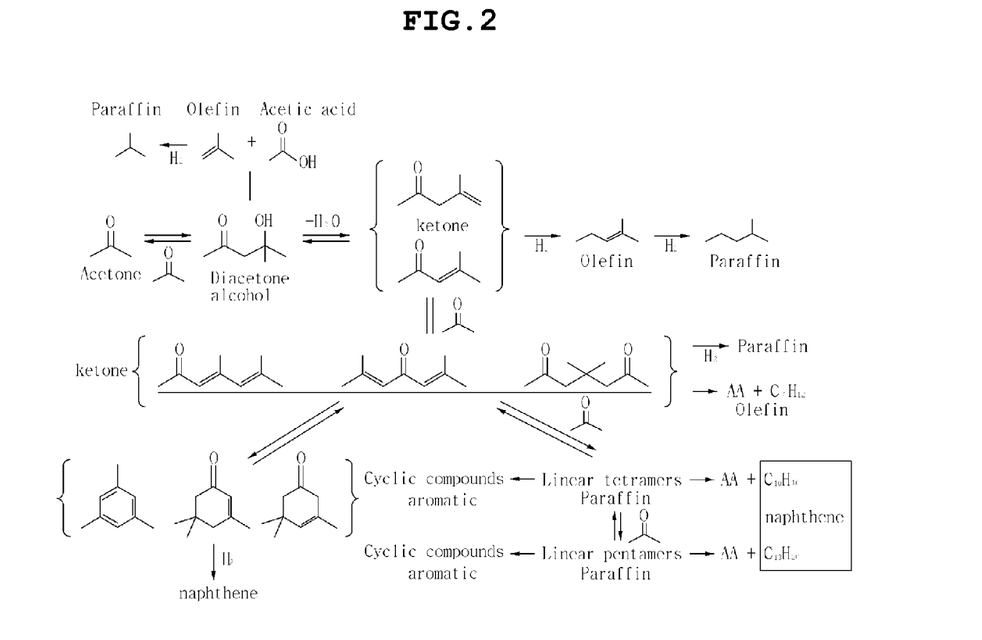
FIG. 2 is a reaction scheme illustrating a series of reaction mechanism for the production of aromatic compounds (mixture) from biomass-derived acetic acid via acetone in the presence of a catalyst, with the concomitant production of by-products.

As shown in the reaction mechanism, acetone largely undergoes aldol-condensation reaction, hydrodeoxygenation, cyclization and decomposition (hydrocracking or hydrogenolysis) in the presence of a catalyst, with the resultant production of various products including aromatics, naphthenic compounds, ketenes, olefins, paraffins, etc. For conversion into aromatics, aldol-condensation, hydrodeoxygenation, and cyclization are required. In this regard, two or more rounds of aldol-condensation are preferably performed to convert acetone into aromatics.

Since a variety of reaction mechanisms shown in FIG. 2 target aromatics (e.g., aromatic compounds convertible into BTX, particularly para-xylene), naphthenic compounds may be regarded as by-products. The naphthenic compounds (particularly monocyclic naphthenic compounds), however, result from the additional hydrogenation of a part of the benzene ring of the aromatics. Hence, the prevention of hydrogenation of the benzene ring by controlling the hydrogenation potential of the catalyst would increase selectivity for aromatics. In contrast, such products as olefins and paraffins may be regarded as substantial by-products because they are independent of the cyclization for forming a benzene ring.

In one embodiment of the present invention, an aldol-condensation reaction by which carbon atoms are built up is fundamentally requisite for the production of aromatics of more carbon atoms from acetone of fewer carbon atoms. As can be seen, the aldol-condensation of acetone or ketone is accomplished through addition between a carbon atom at alpha position of —CO— in one acetone or ketone molecule and the carbon atom of —CO— in another molecule. Two different molecules, each having a —CO— group, may have the potential of undergoing aldol-condensation. That is, the —CO— group that acetone or a ketone intermediate produced by the aldol-condensation of acetone has is a factor for inducing a consecutive aldol-condensation reaction. As such, a —CO— group, if present in intermediates occurring during the conversion reaction process of acetone, can be converted into aromatics (aromatic compounds convertible into BTX) by additional (consecutive) aldol-condensation, but may be directed toward the production of by-products (by excessive linear aldol-condensation, double cyclization, etc.). For the conversion of acetone, therefore, aldol-condensation should be facilitated, but it is necessary to properly control the —CO— group through hydrodeoxygenation so as to suppress excessive reactions or linear aldol-condensation.

It is noticeable that a conventional technique (for example, Korean Patent Unexamined Application Publication No. 2012-41578) discloses a catalytic reaction using acetone as a reactant, but is significantly low in selectivity for aromatics because it targets conversion into paraffins for use as fuel oils or lubricant base oils. Accordingly, the use of a catalyst the activity of which is controlled to convert acetone into aromatics at a high rate with high selectivity for aromatics, together with controlling a reaction condition, is required for increasing the production yield of high value-added aromatic products.

In addition to the aldol-condensation of acetone (at least 3 molecules), cyclization for forming a benzene ring is indispensible for the production of aromatics from acetone.

Further in order to incite a reactant containing an excess of water (aqueous acetone solution) to react, a stable catalyst (that is, a catalyst stable to hydrothermal treatment) that is neither poisoned with water nor collapses at such a relatively high reaction temperature of the aldol-condensation is preferably employed.

In this context, a catalyst that can be responsible for the aldol-condensation and cyclization reactions may be selected from among solid acid catalysts known in the art, for example, inorganic oxides of transition metals such as Nb, Al, Si, Ti, Zr, Mo (e.g., niobia, alumina, silica, titanic, zirconia, etc.), with preference for niobia ($Nb_2O_5$).

The activity of the solid acid catalyst for use in converting acetone into aromatics is affected by the intrinsic acid strength and acid amount that the catalyst has. These acid properties of the solid acid catalyst tend to be determined by the sintering (thermal treatment) temperature of the catalyst. According to an exemplary embodiment, the acid properties are controlled by thermally treating niobia, used as a support of a catalyst for acetone conversion (particularly in an oxygen-containing atmosphere). The temperature of the thermal treatment may be set to be, for example, about 300 to 1000° C., and particularly about 300 to 700° C. When an aqueous acetone solution is used as a reactant, the thermal treatment may be conducted at about 300 to 500° C., and particularly at about 350 to 450° C. In addition, the thermal treatment may continue for about 2 to 12 hrs, and particularly for about 3 to 6 hrs.

In an embodiment of the present invention, a bifunctional catalyst (responsible for aldol-condensation and cyclization; and hydrodeoxygenation) in which a hydrogenation-active ingredient (metal) for hydrodeoxygenation supported to a niobia support (preferably niobia the activity of which is controlled by certain thermal treatments) is used to selectively produce desired aromatics while suppressing side-reactions that may occur during the aldol-condensation.

On the whole, the metallic ingredient for hydrogenation may be selected from among transition metals, for example, Ru, Ni, Pd, Pt, Re, Au, Ag, Cu, Cr, Mn, Fe, Co and a combination thereof. Due to difference in hydrogenation activity from one to another, and interaction with the support niobia combined therewith, the metals have significant influences on the aldol-condensation, hydrodeoxygenation and/or cyclization reactions of acetones (or ketones). For example, Pt or Ni, although exhibiting a high level of acetone conversion rates, is not preferred in terms of the yield of aromatics because it is directed toward the formation of paraffins and olefins.

According to an embodiment of the present invention, a ruthenium (Ru)-supported niobia catalyst is used for the aromatization of acetone to maximize the yield of target aromatics. In this regard, the content of ruthenium (elemental basis) may range from, for example, about 0.1 to 30% by weight, based on the total weight of the catalyst, particularly from about 0.2 to 10% by weight, and preferably from about 0.3 to 2.5% by weight in consideration of the hydrogenation activity of ruthenium. When the content of ruthenium is excessively small, aldol-condensation rather than hydrogenation actively occurs to rapidly increase the carbon number of the final product. On the other hand, an excessive content of ruthenium may cause the completion of hydrogenation prior to the start of aldol-condensation, with the production of final products of small carbon numbers or may induce additional hydrogenation in target aromatics with the increasing production of naphthenic compounds. Hence, it is desired to control the content of ruthenium within the range.

In one exemplary embodiment, the ruthenium in the catalyst may have a metal particle size or crystal size of, for example, from 0.5 nm to 50 nm, particularly from about 1 nm to 20 nm. The metal particle size or crystal size of ruthenium is one of the factors determining hydrogen reduction ability and has an influence on the control of reaction conditions including hydrogen consumption, reaction temperature, hydrogen pressure, etc. Particularly in order to maximize the yield of aromatics with the concomitant suppression of side reactions, it is desirable to adjust the size of ruthenium in the catalyst into the above-mentioned range.

In another exemplary embodiment, niobia may form a composite support in combination with a binder or matrix that aids the molding of the catalyst. As the binder or matrix, alumina, graphite, and silica may be used singly or in combination. Particularly, niobia is combined with a binder before the above-mentioned thermal treatment. The content of the binder is determined in consideration of the acid catalyst property of niobia, and may range from, for example, 5 to 50% by weight on the weight of the support, and particularly from about 5 to 30% by weight.

Meanwhile, reaction conditions for the aromatization of acetone needs to be set so as to maximally increase selectivity for aromatics that can be converted into BTX (particularly p-xylene). In an exemplary embodiment, the reaction temperature may be set within a range of, for example, about 250 to 400° C., and particularly about 300 to 350° C.

Other than a reaction temperature, factors that have influences on acetone conversion include a hydrogen pressure and a hydrogen flow rate. Typically, hydrogenation increases with an increase in hydrogen pressure and hydrogen flow rate. However, when hydrogenation occurs too actively, together with aldol-condensation, during the aromatization of acetone, various by-products such as linear paraffins, olefins, etc. as well as aromatics may be produced. Thus, it is desirable to properly control a hydrogen pressure and a hydrogen flow rate. For instance, a high hydrogen pressure may increase the conversion rate of acetone but may decrease selectivity for aromatics, thus decreasing the total yield. On the other hand, the catalyst may rapidly become inactive under a low hydrogen pressure. Considering these reaction properties, the hydrogen pressure may be determined within a range of, for example, from about 5 to 100 bar, particularly from about 10 to 50 bar, and more particularly from about 15 to 30 bar. The hydrogen flow rate, that is, the molar ratio of hydrogen ($H_2$)/acetone may range from, for example, about 0.5 to 30, particularly from about 1 to 10, and more particularly from about 1 to 5.

In addition, upon a continuous mode, the space velocity (WHSV) may range, for example, from about 0.1 to 10 $h^{-1}$, and particularly from about 0.2 to 2 $h^{-1}$. For a batch-type reaction, the ruthenium-supported niobia catalyst may be used in an amount of about 0.1 to 10 g based on 100 cc of the reactant (acetone acid), and particularly in an amount of about 0.5 to 5 g.

In accordance with one embodiment, the conversion rate of acetone and the selectivity for aromatics vary depending on ruthenium-supported niobia catalyst and conditions (reaction temperature, hydrogen pressure, $H_2$/acetone molar ratio, etc.). Hence, it is desirable to control the individual process conditions such that the acetone conversion rate should be set to be at least about 50% (particularly at least about 60% and more particularly at least 70%) with selectivity for aromatics maintained at about 50% or higher (particularly about 60% or higher, and more particularly about 70% or higher).

As mentioned above, naphthenic compounds can be converted into aromatics when the reaction condition is precisely controlled. In a broad sense, thus, selectivity for target products may be determined in consideration of naphthenic compounds as well as aromatics. In an exemplary embodiment, selectivity for target compounds including aromatics and naphthenic compounds may be at least about 60%, particularly at least about 70%, and more particularly at least 75%.

The by-product olefins may have negative influences on a subsequent process for converting aromatics into high value-added aromatic products, e.g., BTX (particularly p-xylene) (for example, transalkylation process). The reaction conditions are preferably controlled such that the products have an olefinic content of about 3% by weight or less, and particularly about 1% by weight or less.

Aromatics

Figure 3:
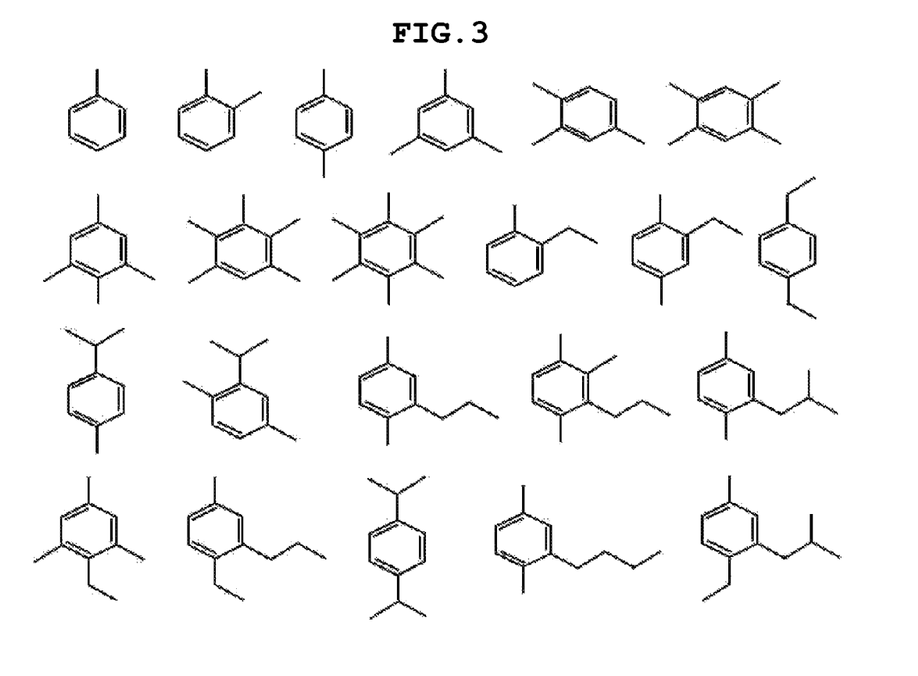
FIG. 3 shows examples of aromatic compounds that can be produced from biomass-derived acetic acid through a series of reactions.

In one embodiment, aromatics produced by acetone conversion reactions are aromatic materials convertible into BTX, particularly para-xylene, and are typically obtained as a mixture. Because the aromatics are formed from acetone by two to four rounds of aldol-condensation, they are monocyclic aromatic compounds of 6 to 15 carbon atoms (particularly, about 8 to 13 carbon atoms), and particularly unsubstituted or mono- or polysubstituted monocyclic aromatic compounds. The substituents may be, for example, $-CH_3$, $-C_2H_5$, $-C_3H_7$, $-C_4H_9$, etc. Examples of the target aromatics are illustrated in FIG. 3. As can be seen, the aromatics include xylene (mixed xylene), trimethyl benzene, tetramethyl benzene, pentamethyl benzene, dimethylethyl benzene, dimethylpropyl benzene, dimethylbutyl benzene, trimethylpropyl benzene, and trimethylbutyl benzene.

Separation of Aromatics

In one embodiment of the present invention, as described above, a water separation process is not required until aromatics are produced because both the acetic acid conversion process and the acetone conversion process are performed in an aqueous phase (an excess of water). However, a water separation process may be taken in order to further utilize the aromatics produced by the acetone conversion reaction. As described above, the resulting products obtained after the aromatization of acetone contain aromatics, unreacted acetone, by-products, and water. The unreacted acetone is present as a solution (an aqueous phase) because it is highly miscible with water. In contrast, aromatics are separated from the aqueous phase (that is, forms an aromatic phase) because of their poor miscibility with water. After completion of the aromatization of acetone, the aromatics, which are the target products, can be recovered through spontaneous phase separation from the unreacted reactant and water.

Subsequent Process (Optional)

According to an exemplary embodiment, the aromatics produced by the acetone conversion contain high value-added aromatics such as BTX, and a significant amount of aromatic compounds of low value is also detected in the recovered products. For this, trans-alkylation may be conducted to convert the aromatic compounds of low value into BTX, particularly para-xylene. Typically, the trans-alkylation occurs in the presence of a catalyst, simultaneously with disproportionation between toluenes, trans-aklylation between toluene and aromatics of C9 or higher, dealkylation between alkylaromatic compounds of C9 or higher, and trans-alkylation between benzene and aromatic compounds of C9 or higher.

The dealkylation produces toluene necessary for the disproportionation/trans-alkylation, while the trans-alkylation between benzene and aromatic compounds of C9 or higher produces toluene and xylene. Meanwhile, the olefins produced by the dealkylation, such as ethylene, propylene, etc., need to be rapidly hydrogenated. If these olefins are not rapidly hydrogenated, they are re-alkylated into aromatics, resulting in decreasing the conversion rate of aromatics of C9 or higher. In addition, olefins themselves undergo polymerization to generate coke, which causes the deactivation of the catalyst.

A catalyst available for the trans-alkylation is disclosed in U.S. Pat. No. 6,867,340 issued to the present applicant, which is hereby incorporated by reference in its entirety into this application. In detail, the catalyst for trans-alkylation comprises a carrier and a hydrogenation metal component supported on the carrier, wherein the carrier comprises (I) about 5 to 90% by weight of either or both of mordenite and beta-type zeolite, having a molar ratio (SAR) of silica to alumina of about 10 to 200, and (II) about 5 to 90% by weight of at least one inorganic binder selected from the consisting of gamma-alumina, silica, silica-alumina, bentonite, kaolin, clinoptilolite and montmorillonite, and the hydrogenation metal contains (i) about 0.001 to 0.5 parts by weight of platinum (Pt) and (ii) about 0.01 to 10.0 parts by weight of at least one selected from the group consisting of tin (Sn), indium and lead, based on 100 parts by weight of the support. According to an exemplary embodiment, a combination of platinum and tin, or platinum and lead may be used wherein tin or lead may be contained in an amount of about 0.01 to 10 parts by weight and in an amount of about 0.01 to 7 parts by weight, respectively.

In one exemplary embodiment, the BTX and the hydrocarbons of 9 or more carbon atoms, produced by the trans-alkylation, are separated from each other by an aromatic separation process. Subsequently, C8 aromatics may be subjected to xylene isomerization. After p-xylene is separated from a mixture of xylenes (o-xylene, m-xylene and p-xyelene), the residues are isomerized to p-xylene. In this regard, the separation of p-xylene form the mixed xylenes may be achieved using well-known processes such as absorption, crystallization, etc. A catalyst for xylene isomerization is described in U.S. Patent Provisional Application No. 12/312,361 of the present applicant, which is hereby incorporated by reference in its entirety into this application.

A better understanding of the present invention may be obtained through the following examples which are set forth to illustrate, but are not to be construed as limiting the present invention.

PREPARATION EXAMPLE 1

Catalyst

After being dried, 80 g of the commercially available niobia ($Nb_2O_5$) catalyst (CBMM) was mixed with PBA (pseudo-boehmite alumina) for 2 hrs using a roll mixer (sold under the nude name of BF-5RM from Dongseo Science Co.). While being added with hydrochloric acid and water incrementally, the mixture of niobia and PBA was kneaded until niobia and PBA were well conglomerated as hydrochloric acid reacted with PBA. The kneaded mixture of niobia and PBA was extruded into thin catalyst threads using an injection machine (in-house made), dried, and pulverized again (size: about 2 to 3 mm). Thereafter, the pulverized particles were sintered at 400° C. for 3 hrs in a furnace. The resulting niobia catalyst is termed Nb.

PREPARATION EXAMPLE 2

Catalyst

The niobia catalyst Nb, obtained in Preparation Example 1, was divided into three aliquots which were then individually mixed for 1 hr using a roll mixer. Separately, an acetone solution of a ruthenium precursor, an aqueous solution of a nickel precursor, and an aqueous solution of a palladium precursor were prepared so that ruthenium (Ru), nickel (Ni), and palladium (Pd) were supported on Nb in an amount of 0.5% by weight, 2.5% by weight, and 0.5% by weight, respectively, on the elemental basis of niobia. The precursors of ruthenium, nickel and palladium were ruthenium acetylacetonate (($C_5H_7O_2$)$_3$Ru, Sigma-Aldrich), nickel nitrate hexahydrate (Ni(NO$_3$)$_2$.6H$_2$O, Sigma-Aldrich), and a 10 wt % palladium nitrate solution (Pd(NO$_3$)$_2$, 10 wt. % solution in 10 wt. % nitric acid). Using an impregnation method, the precursor solutions were supported on niobia. In detail, the precursor solutions were dropwise added over 2 hrs using a spoil to the niobia that was rotated in a roll mixer so that the metal ingredients were allowed to uniformly permeate into the support. After the impregnation, the solvent was evaporated in heated flowing air of about 160° C. from a heat gun, and the dried catalysts were sintered at 350° C. for 3 hrs in a furnace. After the thermal treatment, the catalysts thus obtained were, respectively, named 0.5 Ru/Nb, 2.5 Ni/Nb, and 0.5 Pd/Nb according to the supported metals and their contents. In case of the 0.5 Ru/Nb catalyst, it is simply termed Rb/Nb unless it is stated together with the other metal-supported catalysts.

EXAMPLE 1

Preparation of Aqueous Acetic Acid Solution

For use in the Example, commercially available acetic acid (purity 99% or higher) was dissolved in water to give a model solution.

Conversion of Acetic Acid into Acetone

Figure 4:
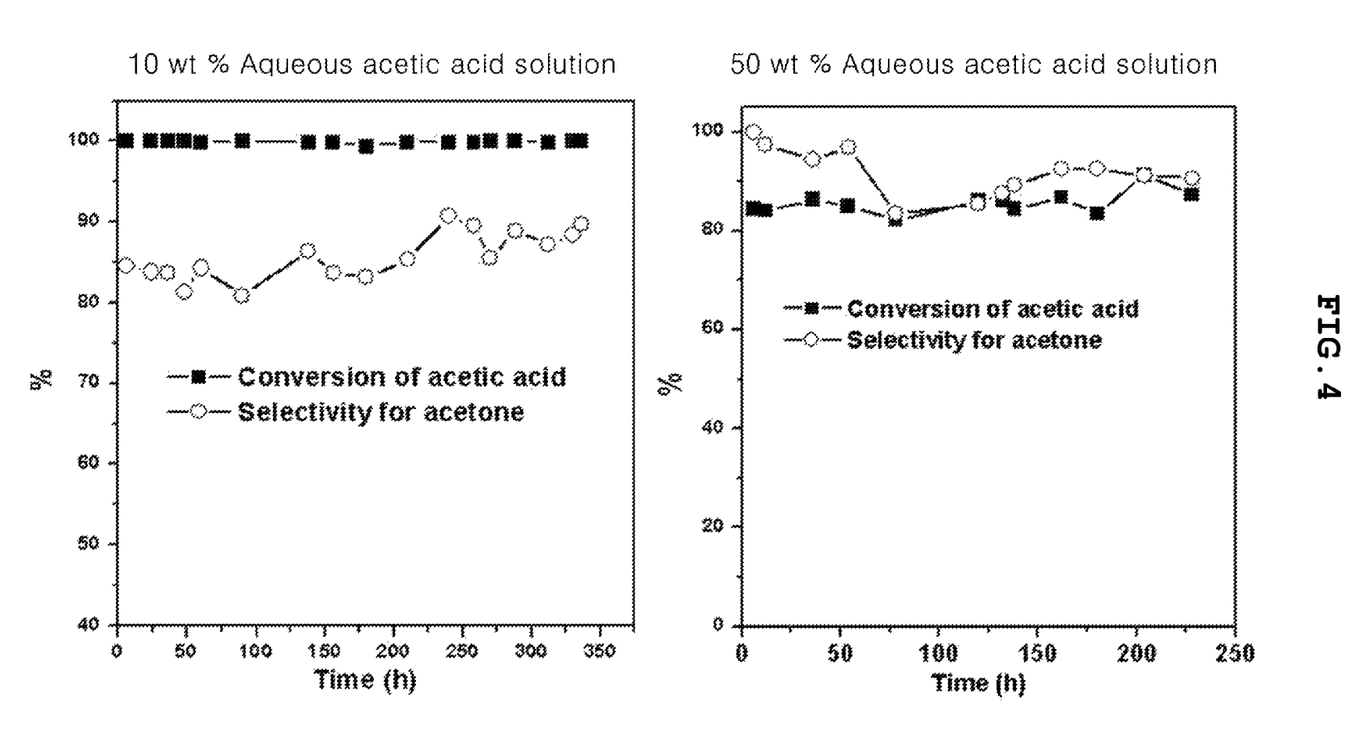
FIG. 4 shows graphs in which conversion rates of acetic acid and selectivity for acetone are plotted with time when acetic acid is converted into acetone in aqueous phases of two concentrations (10 wt % and 50 wt %) in the presence of a catalyst in accordance with Example 1.

Aqueous acetic acid solutions with two concentrations (10 wt % and 50 wt %) were introduced into respective continuous flow reactors, each filled with 6 g of a zirconia catalyst. The reaction was conducted at a temperature of 350° C., a pressure of 5 bar, and a space velocity (WHSV) of 1 h$^{-1}$ under a stream of nitrogen. The results are shown in FIG. 4. As can be seen, the acetic acid in aqueous solutions was converted into acetone at a rate of about 80% or greater, and higher conversion rates were obtained in aqueous acetic acid solutions of lower concentrations (a conversion rate approaching to 100% in a 10 wt % aqueous solution). In addition, selectivity for acetone was observed to be maintained at about 80 to 90% even after the reaction time had passed.

EXAMPLE 2

Figure 5:
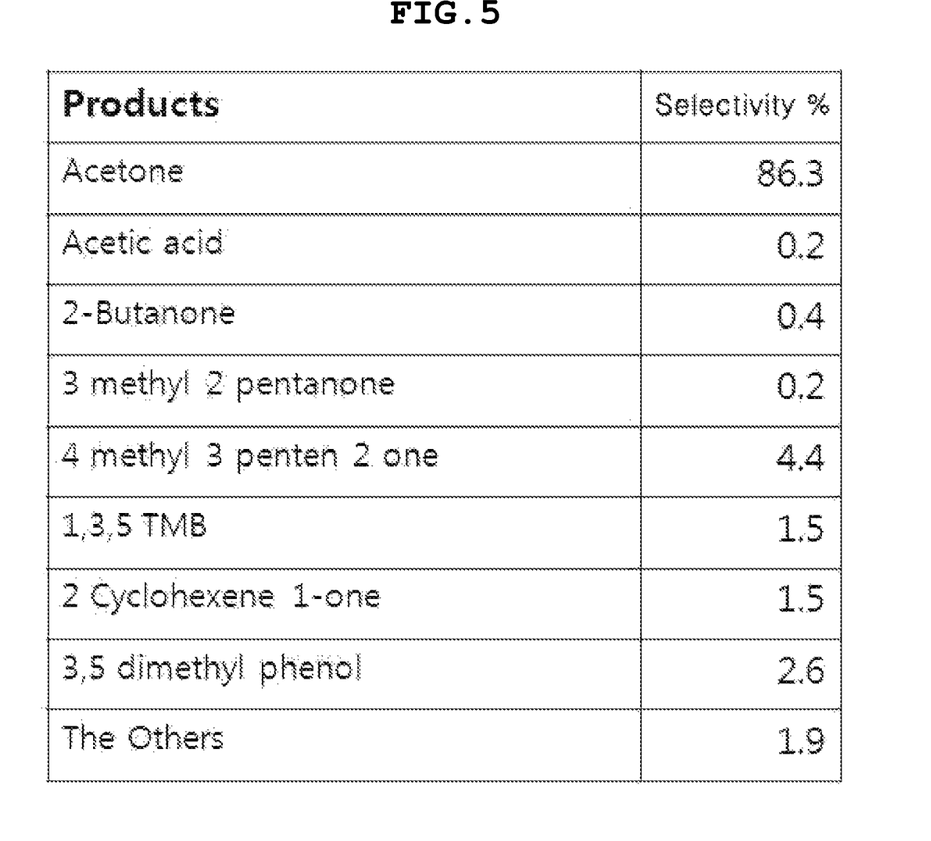
FIG. 5 is a table that summarizes the composition (selectivity) of the products obtained by converting calcium acetate into acetone through pyrolysis in accordance with Example 2.

In a reactor (in-house made), 100 g of calcium acetate (Sigma Aldrich) was pyrolyzed at 420° C. The composition of the pyrolyzate is shown in FIG. 5. As can be seen, the conversion rate of calcium acetate and selectivity for acetone were 95% or higher and 85% or higher, respectively, at 420° C. In addition to acetone, C4, C5, and C6 ketones were produced.

EXAMPLE 3

Catalyst Screening

In this Example, the niobia catalyst prepared in Preparation Example 1 and the three different metal-supported niobia catalysts (Nb, 0.5 Ru/Nb, 2.5 Ni/Nb, and 0.5 Pd/Nb) prepared in Preparation Example 2 were used. In addition, a 50 wt % aqueous acetone solution was used as a reactant to determine whether acetone in an aqueous phase could be converted into aromatics.

In an in-house made reactor, the aromatization of acetone was performed over 48 hrs under conditions including a temperature of 320° C., a hydrogen pressure of 50 bar, a space velocity (WHSV) of 0.4 h$^{-1}$, and a H$_2$/acetone molar ratio of 3.8. The results are shown in Table 1 and FIG. 6.

TABLE 1

| Catalyst | Acetone Conversion rate (%) | Selectivity for Aromatics[1] + Naphthenic Compound[2] (%) |
|---|---|---|
| Nb (Comparative) | 36.2 | 78.1 |
| 0.5Ru/Nb (Inventive) | 98.1 | 71.6 |
| 2.5Ni/Nb (Comparative) | 89.2 | 20.7 |
| 0.5Pd/Nb (Comparative) | 99.3 | 23.9 |

Figure 6:
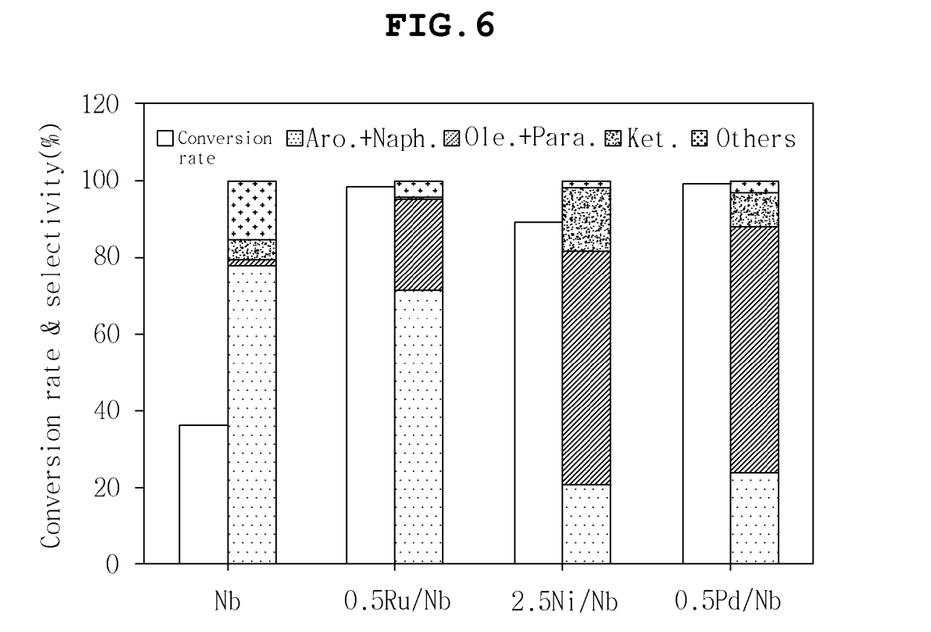
FIG. 6 is a graph showing conversion rates of acetone and selectivity for components of aromatized products according to catalysts when acetone in an aqueous phase is converted into aromatic compounds in the presence of four different catalysts (Nb, Ru/Nb, Ni/Nb, and Pd/Nb) under the condition set in Example 3 (temperature: 320° C., pressure: 50 bar ($H_2$), WHSV: 0.4 $hr^{-1}$, $H_2$/acetone: 3.8)

[1]monocyclic aromatic compound convertible into BTX
[2]naphthenic compounds produced as monocyclic aromatic compounds convertible into BTX are hydrogenated to remove the double bond of the benzene ring As can be seen in Table 1 and FIG. 6, aromatic compounds convertible into BTX were produced from all the aromatic reactions of acetone using the four catalysts. However, the four different catalysts were different in aromatization activity from one to another. Particularly, the Nb catalyst free of hydrogenation metals exhibited an acetone conversion rate of 36.2% while the three metal-supported catalysts (0.5 Ru/Nb, 2.5 Ni/Nb, and 0.5 Pd/Nb) achieved conversion rates of as high as 98.1%, 89.2% and 99.3%, respectively. As such, the hydrogenation metal, when supported on Nb, was observed to play a positive role in improving the conversion rate of the niobia catalyst.

In Table 1 and FIG. 6, selectivity for naphthenic compounds (convertible into aromatic compounds by controlling hydrogenation) as well as aromatics is given. In FIG. 6, olefins and paraffins are regarded as by-products.

Selectivity for aromatic and naphthenic compounds were measured to be 78.1% and 71.6% in the Nb catalyst and the Ru/Nb catalyst, respectively, and 20.7% and 23.9% in the Ni/Nb catalyst and the Pd/Nb catalyst, respectively. Thus, the latter catalysts are not suitable for the aromatization of acetone. This is attributed to the fact that, in the presence of the nickel- or palladium-supported catalyst, a part of the intermediates after the aldol-condensation of acetone is cyclized, but most of the intermediates are hydrogenated in a linear state. The products from the conversion of acetone in the presence of nickel- or palladium-supported catalyst in this Example were analyzed to contain a great amount of paraffins and olefins of 12 carbon atoms (up to 15 carbon atoms for the palladium-supported catalyst. As such, the aldol-condensation was estimated to be linearly conducted in the nickel- or palladium-supported catalyst.

In addition, the Nb catalyst was preferable in selectivity for aromatics, but exhibited an acetone conversion rate of 36.2%, thus decreasing the overall yield of aromatics, compared to the Ru/Nb catalyst.

EXAMPLES 4 AND 5

The aromatization of acetone was performed in the same condition as in Example 3, with the exception that the Ru/Nb catalyst prepared in Preparation Example 2 was employed and the hydrogen pressure was reduced to 20 bar to prevent naphthenic compounds from being produced due to excessive hydrogenation (Example 4), and with the exception that the hydrogen pressure was reduced to 20 bar and the reaction temperature was altered to 350° C. (Example 5). After aromatization for 48 hrs, reaction results are shown in Table 2 and FIG. 7. For comparison, results of Example 3 are also given.

TABLE 2

| Rxn Condition | Acetone Conversion Rate (%) | Selectivity for Aromatics (%) | Selectivity for Naphthenic Cpd. (%) | Selectivity for Paraffins and Olefins (%) |
|---|---|---|---|---|
| 320° C., 50 bar (Ex. 3) | 98.1 | 24.7 | 46.9 | 23.9 |
| 320° C., 20 bar (Ex. 4) | 77.1 | 55.9 | 22.2 | 6.8 |
| 350° C., 20 bar (Ex. 5) | 90.5 | 75.9 | 12.2 | 7.3 |

Evaluation for Effect of Hydrogen Pressure

Figure 7:
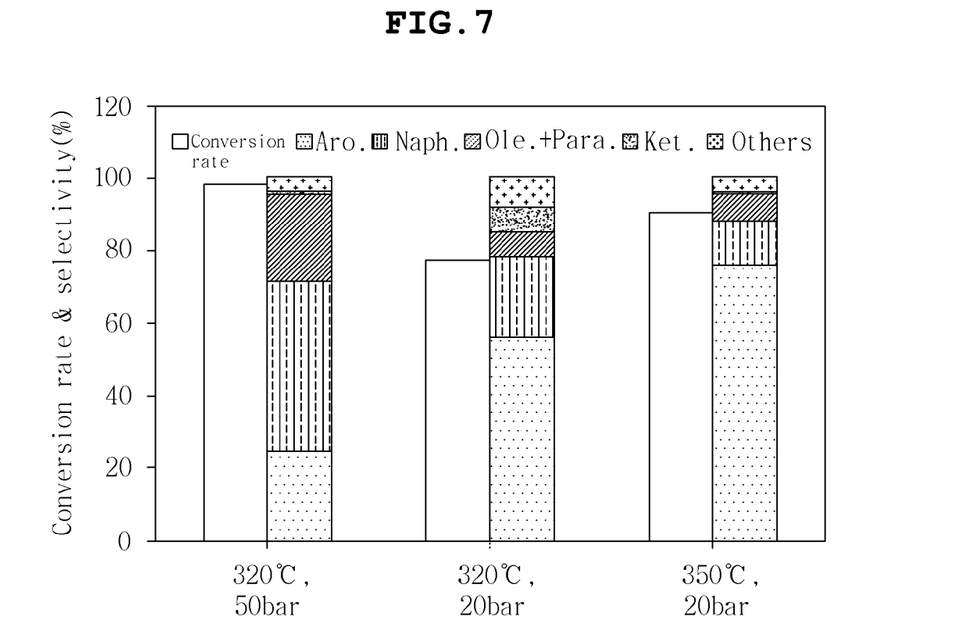
FIG. 7 is a graph showing conversion rates of acetone and selectivity for components of aromatized products according to reaction pressure and temperature in the presence of the Ru/Nb catalyst under the conditions set in Examples 3 to 5 (WHSV: 0.4 $h^{-1}$, $H_2$/acetone: 3.8)

As is understood from the data of Table 2 and FIG. 7, selectivity for aromatics was greatly increased from 24.7% to 55.9% as the hydrogen pressure decreased from 50 bar to 20 bar. This change indicated that the hydrogen pressure has a significant influence on the aromatization of acetone by the Ru/Nb catalyst. It is noticeable that selectivity for naphthenic compounds was greatly decreased (from 46.9% to 22.2%) with a decrease in hydrogen pressure. In addition, although the hydrogen pressure was reduced, selectivity for the overall cyclized products of aromatics and naphthenic compounds were increased from 71.9% to 78.1%. From the experiment data, it is understood that reducing the hydrogen pressure to a certain level is advantageous for the aromatization of acetone. But, the data also indicate that when the hydrogen pressure is reduced too much, an excessive aldol-condensation occurs, with the concomitant production of compounds of a large number of carbon atoms. As a result, the concentration of relatively light aromatic compounds (monocyclic aromatic compounds) convertible into BTX is reduced, which is undesirable in terms of selectivity. Particularly, since heavy molecules of large numbers of carbon atoms that are produced by double cyclization, such as indane or naphthalenic compounds, may act as a catalyst poison, the catalyst may be deactivated at too a low hydrogen pressure.

As the hydrogen pressure decreased from 50 bar to 20 bar, the conversion rate of acetone was reduced from 98.1% to 77.1%. The catalytic activity was not regarded as being attenuated as the hydrogen pressure decreased. The result was considered to be attributed to the fact that the portion of acetone participating in the formation of linear by-products such as paraffins and olefins was reduced as shown in Table 3 and FIG. 7 (selectivity for paraffins and olefins were decreased from 23.9% to 6.8%).

Evaluation for Effect of Reaction Temperature

As is understood from data of Table 2 and FIG. 7, an increase of the reaction temperature as in Example 5 (at a hydrogen pressure of 20 bar: reaction temperature increased from 320° C. to 350° C.) resulted in an increase in the conversion rate of acetone from 77.1% to 90.5% and in selectivity for BTX-convertible aromatics from 55.9% to 75.9%. In addition, selectivity for monocyclic aromatic and naphthenic compounds was also increased from 78.1% to 88.1%.

As proven above, the overall catalytic activity was observed to increase with an increase in the reaction temperature. In order to apply the product to aromatic products such as BTX, however, it is necessary to reduce the content of olefins in the product. At 350° C., the product was analyzed to have an olefinic content of about 2.6 wt %, indicating that an increase of the reaction temperature is advantageous for the catalytic activity, but may be prone to generate olefins that are disadvantageous for a subsequent process for conversion into BTX. Therefore, it is desired that the upper limit of the reaction temperature be properly set.

EXAMPLE 6

Evaluation for Effect of Hydrogen Volume ($H_2$/Acetone Molar Ratio)

The aromatization of acetone was performed for 48 hrs under the same condition as in Example 4, with the exception that the $H_2$/acetone molar ratio was set to be 1.5. The results are given in Table 3 and FIG. 8. For comparison, the results of Example 4 are also shown.

TABLE 3

| | | Selectivity for | | | |
|---|---|---|---|---|---|
| $H_2$ Flow Rate | Acetone Conversion Rate (%) | Aromatics (%) | Naphthenic Cpd. (%) | Paraffins and Olefins (%) | ketones (%) |
| $H_2$/acetone Molar ratio = 3.8 (Ex. 4) | 77.1 | 55.9 | 22.2 | 6.8 | 7.1 |
| $H_2$/acetone Molar ratio = 1.5 (Ex. 6) | 79.3 | 91.4 | 0 | 1.8 | 1 |

Figure 8:
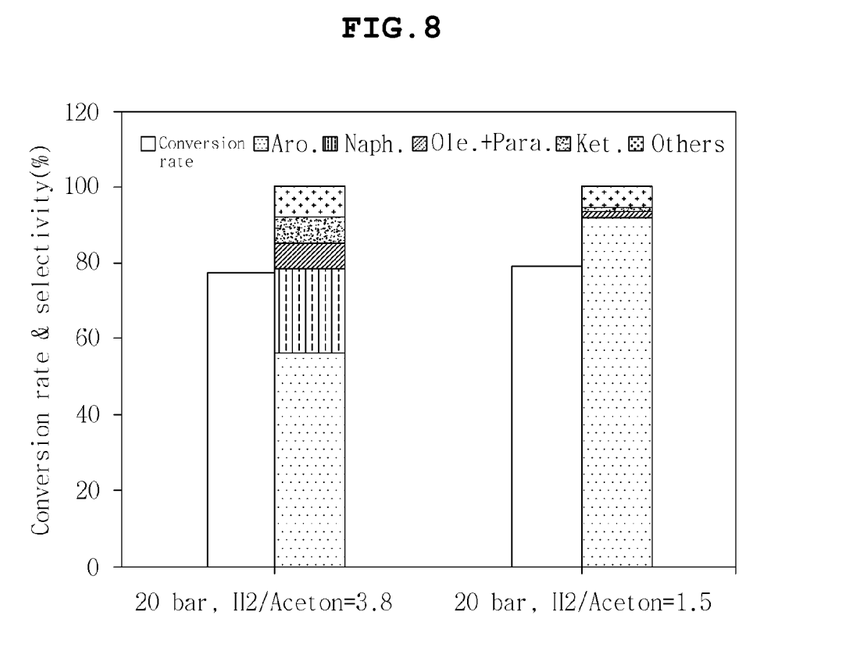
FIG. 8 is a graph showing conversion rates of acetone and selectivity for components of aromatized products according to $H_2$/acetone molar ratio under the conditions set in Examples 4 and 6 (temperature: 320° C., pressure: 20 bar ($H_2$), WHSV: 0.4 $hr^{-1}$)

As can be seen in Table 3 and FIG. 8, a decrease in $H_2$/acetone molar ratio did not cause a substantial change in the conversion rate of acetone, but resulted in a significant difference in the composition of the product. Particularly, as the $H_2$/acetone molar ratio decreased, selectivity was significantly increased from 55.9% to 91.4% for BTX-convertible aromatics, but decreased from 22.2% to 0% for naphthenic compounds, suggesting that after being produced, the aromatics did not undergo hydrogenation into naphthenic compounds.

Also, selectivity for overall cyclization products (monocyclic aromatic compounds and naphthenic compounds derived therefrom increased from 78.1% to 91.4%. Hence, when the hydrogen flow rate is controlled, the linear aldol-condensation and the resultant hydrogenated products (ketones, paraffins and olefins) are found to decrease in overall level.

Derivation of Optimal Conditions for Acetone Conversion

As described above, there are various factors that have influences on the aromatization of acetone. Particularly, the niobia catalyst (Nb) alone exhibited good selectivity for aromatics useful as high value-added aromatic products, but a poor conversion rate of acetone. On the other hand, the Ru/Nb catalyst in which ruthenium was supported as a metal hydride on niobia was found to allow for an improved yield of aromatics, compared to other catalysts (Ni, Pd, etc.).

The following conclusion was derived from various experiments in which the Ru/Nb catalyst was used under various reaction conditions (particularly, in aqueous solutions).

First, the conversion rate of acetone and selectivity for target aromatics were increased as the hydrogen pressure was reduced if it was above a critical point at which the catalyst was deactivated.

Second, an increase in reaction temperature increased the conversion rate of acetone and selectivity for target aromatics, but resulted in producing olefins that might act as an obstacle to subsequent processes.

Third, the catalytic activity was increased as the hydrogen flow rate to the reactant acetone was decreased, which was coincident with the result from the experiment with hydrogen pressures. However, the effect of hydrogen flow rate on aromatization was considered larger than that of hydrogen pressure. Particularly, selectivity for paraffins, olefins and ketones as well as naphthenic compounds was reduced simultaneously at a lower hydrogen flow rate.

Figure 9:
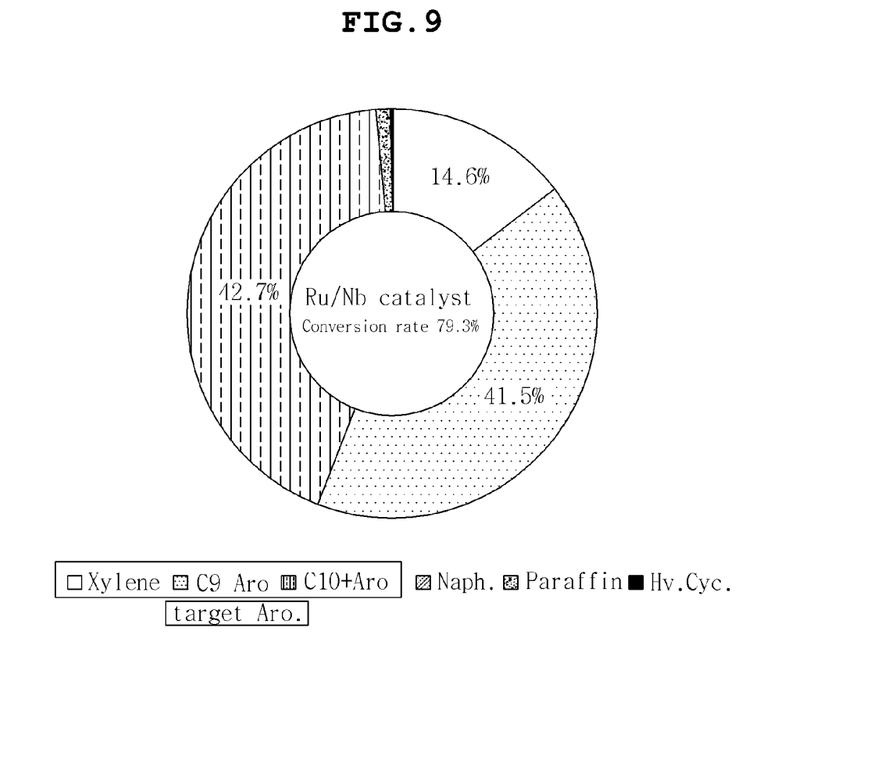
FIG. 9 is a view showing conversion rates of acetone and composition of (selectivity for) components of aromatized products when acetone is converted under the optimal condition established from the data of Examples 3 to 6.

Finally, in full consideration of a change in the activity behavior of the Ru/Nb catalysis according to reaction conditions (Examples 3 to 6; Tables 1 to 3 and FIGS. 6 to 8), the most catalytic activity in terms of the conversion rate of acetone and selectivity for aromatics was obtained under the reaction condition of a reaction temperature of about 320° C., a hydrogen pressure of about 20 bar and a $H_2$/acetone molar ratio of 1.5 (Example 6). The composition of the product obtained under the optimal condition is depicted in FIG. 9.

EXAMPLE 7

Evaluation for Short-Term Durability Ru/Nb Catalyst in Acetone Conversion

Under the optimal condition established in Example 6, the Ru/Nb catalyst was evaluated for short-term durability in acetone conversion (aromatization). The catalytic activity (yield) of the Ru/Nb catalyst is plotted with reaction time in FIG. 10.

Figure 10:
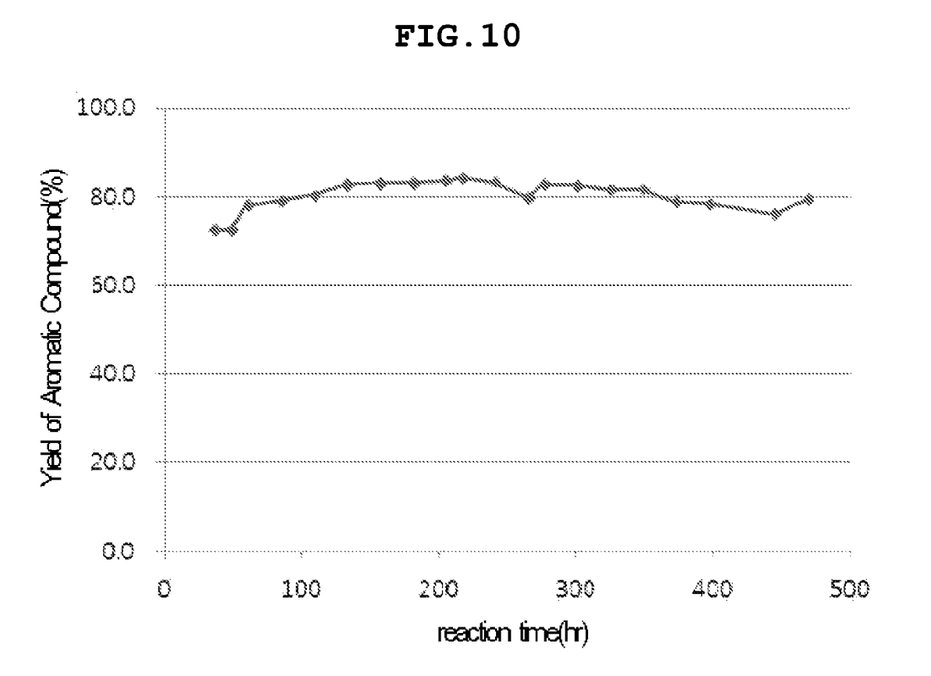
FIG. 10 is a graph showing short-term durability test results of the Ru/Nb catalyst during acetone conversion according Example 7.

As can be seen in FIG. 10, the Ru/Nb catalyst retained uniform activity over about 480 hrs (20 days) during which the catalyst was evaluated for short-term durability. Briefly, after the stabilization time of first 50 hrs, the Ru/Nb catalyst was observed to produce monocyclic aromatics convertible into BTX, particularly p-xylene, at a yield of about 80% over about 20 days, with being little deactivated. This was believed to be attributed to the fact that, upon the acetone conversion under the optimal condition established in Example 6, the production by-products, such as indane and naphthenic compounds, which were anticipated to have negative influences on the acetone conversion, were maximally suppressed.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for producing an aromatic compound from acetic acid, comprising:
    a1) providing acetic acid;
    b1) converting said acetic acid into an acetate salt; pyrolyzing the acetate salt to an acetone; and
    c1) converting the acetone into an aromatic compound in the presence of a ruthenium-supported niobia catalyst (Ru/Nb);
    wherein the ruthenium-supported niobia catalyst (Ru/Nb) contains ruthenium in an amount of 0.3 to 2.5% by weight on an elemental basis.

2. The method of claim 1, wherein the acetic acid is biomass-derived acetic acid.

3. The method of claim 1, wherein the ruthenium of the ruthenium-supported niobia catalyst has a particle size or crystal size of 1 to 20 nm.

4. The method of claim 1, wherein the niobia of the ruthenium-supported niobia catalyst is thermally treated at 300 to 1000° C.

5. The method of claim 1, wherein step c1) is conducted at a temperature of 250 to 400° C., a hydrogen pressure of 5 to 100 bar, and a hydrogen ($H_2$)/acetone molar ratio of 0.5 to 50.

6. The method of claim 5, wherein step c1) is conducted at a space velocity (WHSV) of 0.1 to 10 $h^{-1}$ in a continuous mode, or is conducted in the presence of 0.1 to 10 g the ruthenium-supported niobia catalyst based on 100 cc of acetone in a batch mode.

7. The method of claim 6, wherein the acetone is converted into acetone at a rate of at least 50% with a selectivity for aromatic compounds of at least 50% in step c1).

8. The method of claim 7, wherein the aromatic compound further comprises naphthenic compound and olefinic compound and wherein overall selectivity for aromatic and naphthenic compounds is at least 60% in step c1), with an olefinic content of 3 wt % or less in the product of step c1).

9. The method of claim 1, wherein the aromatic compound is a monocyclic aromatic compound having 6 to 15 carbon atoms.

10. The method of claim 9, wherein the aromatic compound is an unsubstituted, mono- or polysubstituted monocyclic aromatic compound, the substituent being —$CH_3$, —$C_2H_5$, —$C_3H_7$, or —$C_4H_9$.

11. The method of claim 10, wherein the aromatic compound is selected from the group consisting of xylene, trimethyl benzene, tetramethyl benzene, pentamethyl benzene, dimethylethyl benzene, dimethylpropyl benzene, dimethylbutyl benzene, trimethylpropyl benzene, and trimethylbutyl benzene.

12. The method of claim 1, further subjecting the recovered aromatic compound to trans-alkylation to obtain an aromatic product selected from the group consisting of benzene, toluene, and xylene.

13. The method of claim 12, wherein the xylene is divided into para-xylene and other xylenes, followed by isomerizing the other xylenes into para-xylene.

14. The method of claim 1, wherein the acetate is calcium acetate.

15. A method for producing an aromatic compound from biomass-derived acetic acid, comprising:
    a2) providing an aqueous solution containing the biomass-derived acetic acid;
    b2) reacting the aqueous solution containing the biomass-derived acetic acid in presence of a catalyst selected from the group consisting of zirconia, titania, alumina, silica, silica-alumina to give an acetone-containing aqueous solution; and
    c2) converting the acetone of the acetone-containing aqueous solution into an aromatic compound in presence of a ruthenium-supported niobia catalyst (Ru/Nb); and d2) separating water from the product of step c2) to recover the aromatic compound,
wherein the ruthenium-supported niobia catalyst (Ru/Nb) contains ruthenium in an amount of 0.3 to 2.5% by weight on an elemental basis.

16. The method of claim 15, wherein the acetic acid-containing aqueous solution of step a2) has an acetic acid concentration of 1 to 90 wt %, and the acetone-containing aqueous solution of step b2) has an acetone concentration of 1 to 90 wt %.

17. The method of claim 15, wherein step c2) is carried out at a temperature of 250 to 400° C., a hydrogen pressure of 5 to 100 bar, and a hydrogen ($H_2$)/acetone molar ratio of 0.5 to 50.

18. The method of claim 17, wherein step c2) is conducted at a space velocity (WHSV) of 0.1 to 10 h$^{-1}$ in a continuous mode, or is conducted in the presence of 0.1 to 10 g of the ruthenium-supported niobia catalyst based on 100 cc of acetone in a batch mode.

19. The method of claim 18, wherein the acetone is converted into acetone at a rate of at least 50% with a selectivity for aromatic compounds of at least 50% in step c2).

20. The method of claim 19, wherein the aromatic compound further comprises naphthenic compound and olefinic compound and wherein overall selectivity for aromatic compound and naphthenic compounds is at least 60% in step c2), with an olefinic content of 3 wt % or less in the product of step c2).

21. The method claim 15, wherein an aromatic compound is recovered from the product of step c2) by phase separation in step d2).

22. The method of claim 15, wherein steps b2) to d2) are carried out consecutively in a single reactor.

23. The method of claim 15, wherein the ruthenium of the ruthenium-supported niobia catalyst has a particle size or crystal size of 1 to 20 nm.

24. The method of claim 15, wherein the niobia of the ruthenium-supported niobia catalyst is thermally treated at 300 to 1000° C.

25. The method of claim 15, wherein thee aromatic compound is a monocyclic aromatic compound having 6 to 15 carbon atoms.

26. The method of claim 15, further subjecting the recovered aromatic compound to trans-alkylation to obtain an aromatic product selected from the group consisting of benzene, toluene, and xylene.

* * * * *